US005571709A

United States Patent [19]

Devauchelle et al.

[11] Patent Number: 5,571,709

[45] Date of Patent: Nov. 5, 1996

[54] MODIFIED BACULOVIRUS AND BACULOVIRUS EXPRESSION VECTORS

[75] Inventors: Gérard Devauchelle; Martine Cerutti, both of Saint-Christol-Les-Ales; Claire Cahoreau, Nimes, all of France

[73] Assignee: Institut National de la Recherche Agronomique, Paris, France

[21] Appl. No.: 966,197

[22] PCT Filed: Jul. 17, 1991

[86] PCT No.: PCT/FR91/00588

§ 371 Date: Jun. 1, 1993

§ 102(e) Date: Jun. 1, 1993

[87] PCT Pub. No.: WO92/01801

PCT Pub. Date: Feb. 6, 1992

[30] Foreign Application Priority Data

Jul. 18, 1990 [FR] France .................................. 90 09143

[51] Int. Cl.$^{6}$ ............................. C12N 15/86; C12N 7/00

[52] U.S. Cl. .................................... 435/235.1; 435/320.1; 435/172.1; 435/172.3; 435/69.1

[58] Field of Search ............................... 435/320.1, 69.1, 435/172.1, 172.3, 235.1

[56] References Cited

PUBLICATIONS

Qin et al. "Studies on the Control Region of the p/o Gene of the *Autographs calfornica* Nuclear Polyhedrosis Virus" J. Gen. Virol., vol. 70, pp. 1273–1279, 1989.

Weyer et al. "Analysis of the Promoter of the *Autographs cablfrnica* Nuclear Polyhedrosis Virus p. 10 Gene", J. Gen. Virol., vol. 70, pp. 203–208, 1989.

Vatrou et al. "*Bombyx morie* Nuclear Polyhedrous virus–based vectors for expressing pasenger genes in silkworm cells under viral or cellalar promoter control", Gens, vol. 75, pp. 59–71, 1989.

Hassan Chaabifi, "Investigation of the Regulation of p. 10 and polyhedrin genes of the *Autographs californica* baculoviues and development of new vectors for expressing foreign genes", Ph.D. Theais Univeisite I'Aix–Marseille 2, France, 1992, Abstact.

van Oers et al. "Expression of the *Autographs californica* nuclear polyhedrosis virus p. 10 gene: effect of polyhdedrin gene expression", Arch. Virol. (1992), vol. 123, pp. 1–11.

*Primary Examiner*—David Guzo
*Attorney, Agent, or Firm*—Dickinson, Wright, Moon, Van Dusen & Freeman

[57] ABSTRACT

The invention relates to a modified baculovirus wherein one of the two strong late promoters of the wild baculovirus is inactive, as well as to a method for obtaining such a modified baculovirus and to its application for obtaining vectors for the expression of exogenous genes. Said modified baculovirus is particularly deprived of the polyhedrin gene promoter and contains the protein P10 gene promoter.

12 Claims, No Drawings

MODIFIED BACULOVIRUS AND BACULOVIRUS EXPRESSION VECTORS

The present invention relates to expression vectors obtained from modified baculoviruses, in which one of the two strong late promoters of the wild-type baculovirus is inactive.

BACKGROUND OF THE INVENTION

Baculoviruses are currently used in a very large number of laboratories as vectors for the expression of genes. In effect, these viruses possess the following advantages: they permit the insertion of long segments of DNA and possess, in addition, two strong late promoters, the polyhedrin promoter and the P10 protein promoter, which are capable of inducing an extremely high level of expression of the genes placed under their control.

The publication of L. K. MILLER [CHAPTER 14 "A VIRUS VECTOR FOR GENETIC ENGINEERING IN INVERTEBRATES" of the manual "GENETIC ENGINEERING IN THE PLANT SCIENCES" (1981) N. J. PANAPOULOS, ed., Praeger Pub. New York, p. 203–224] describes the advantages of the use of baculoviruses, and especially of the baculovirus *Autographa californica* (AcNPV), as vectors for the expression of foreign genes in insect host cells. The AcNPV baculovirus described in this publication possesses two mature forms, referred to as the non-occlusive form (NOV) and the occlusive form (OV), respectively. The non-occlusive forms are responsible for transmission of the virus in cell culture or within the same organism. The occlusive forms are responsible for transmission of the virus from one organism to another. These occlusive forms consist of virions sheathed in a crystalline protein matrix consisting essentially of a single protein: polyhedrin.

It was demonstrated that the polyhedrin gene possessed an exceptionally strong promoter which enabled a high level of expression of the gene placed under its control to be effected. MILLER hence points out that it would be especially advantageous to use baculoviruses as expression vectors, inserting under the control of the polyhedrin promoter the exogenous DNA which it is desired to express.

Other work [SMITH and SUMMERS, J. Virol. 45, 215–225 (1983)] showed that the AcNPV virus possessed another strong late promoter, which is the promoter of the 10 kDa polypeptide or P10 protein.

In addition, the capsid of baculoviruses can contain large amounts of DNA, and hence does not constitute a limit to the number of genes inserted or to their length. Consequently, a very large number of expression vectors derived from baculoviruses have been proposed. For example, European Patent Application 127,839 (SUMMERS invention) describes a method enabling a recombinant expression vector derived from baculovirus to be produced, proceeding via a transfer vector containing a viral DNA fragment containing the polyhedrin gene promoter, downstream of which the foreign gene is inserted. This transfer vector is then recombined with wild-type baculovirus DNA, and the recombinants possessing the foreign gene under the control of the polyhedrin promoter are selected.

European Patent Application 340,359 (inventors PAGE and ROGERS) describes transfer vectors derived from baculoviruses, in which the polyhedrin ATG initiation codon is eliminated, so that the sequence coding for polyhedrin cannot be translated, and which carries a restriction site suitable for insertion of an exogenous gene downstream of the N-terminal end of the polyhedrin gene, and in immediate proximity to the said end.

The Inventors' team has previously developed a method for producing a modified baculovirus which is usable as an expression vector, in which a suitable restriction site is inserted directly, and without recourse to a transfer vector, downstream of a strong late promoter. The vector thereby obtained may be loaded, at the position of the restriction site introduced, with the gene which it is desired to have expressed; this method forms the subject of European Patent Application 345,152.

In all the known methods, the gene to be expressed is inserted under the control of one of the two strong late promoters present in the genome of the wild-type baculovirus, while the other promoter continues to function normally.

Some constructions derived from baculoviruses by inactivation of a strong late promoter are known in the prior art; RANKIN et al. [GENE, 70, 39–49 (1988)] describe various mutations of the polyhedrin promoter having the effect of inhibiting, in varying degrees, the expression of a gene placed under the control of the said promoter. IATROU et al. [GENE, 75, 59–71 (1989)] describe the production of baculovirus in which the polyhedrin promoter has been inactivated by deletion. They propose the use of these baculoviruses as transfer vectors for obtaining constructions in which it is desired to place an exogenous gene under the control of its own promoter, and not under that of the polyhedrin promoter.

Constructions in which the P10 protein promoter is inactive have also been carried out; thus, QUIN et al. [J. Gen. Virol. 70, 1273–1280 (1989)] describe recombinant plasmids comprising constructions in which an exogenous gene is placed under the control of various mutants of the P10 promoter. Some of these mutations have the effect of completely inactivating the promoter.

However, these constructions have been carried out only on recombinant plasmids. In effect, the P10 gene promoter overlies a portion of the sequence coding for the P26 protein, and it is generally considered that a mutation in this promoter does not permit viable baculoviruses to be obtained.

Moreover, it has been proposed, in order to increase gene expression in expression vectors derived from baculoviruses, to multiply, in the same vector, the copy number of the gene and the number of promoters. For example, European Patent Application 0,127,839 suggests inserting, in the same baculovirus, copies of a gene under the control of the polyhedrin promoter, other copies under the control of the P10 promoter and, where appropriate, yet further copies at other positions of the genome, each copy of the said gene being under the control of a baculovirus promoter or alternatively of its own promoter.

SUMMARY OF THE INVENTION

In point of fact, the Inventors have discovered, unexpectedly, that the elimination or inactivation of one of the two strong late promoters of the wild-type baculovirus resulted in an increase in the expression of the gene placed under the control of the remaining promoter.

The aim of the present invention is to provide for [sic] new expression vectors, constructed from modified baculoviruses and in which only one of the two late promoters present in the wild-type baculovirus is active.

The subject of the present invention is expression vectors, characterised in that it [sic] are obtained from a modified baculovirus in which one of the two strong late promoters present in the genome of the wild-type baculovirus is inactive, and in that the sequence placed under the control of the strong late promoter which is active in the said modified baculovirus is different from the corresponding sequence of the wild-type baculovirus.

In the sense of the present invention, "sequence different from the corresponding sequence of the wild-type baculovirus" means, in particular that the sequence which, in the wild-type baculovirus, is controlled by the promoter in question has been subjected to modifications directed towards permitting the expression of an exogenous gene under control of the said promoter. Such modifications comprise, for example, the insertion of an exogenous sequence (gene which it is desired to have expressed, sequence carrying one or more restriction sites, and the like) into the said sequence of the wild-type baculovirus, or in place of all or part of this sequence.

DESCRIPTION OF THE PREFERRED EMBODIMENTS

According to a preferred embodiment of an expression vector according to the invention, the inactive promoter is that of the polyhedrin gene and the active promoter is that of the P10 protein gene.

According to another preferred embodiment of an expression vector according to the invention, the inactive promoter is that of the P10 protein gene and the active promoter is that of the polyhedrin gene.

The subject of the invention is also modified baculoviruses which are usable for obtaining expression vectors such as are defined above.

In this context, the invention encompasses infectious, modified baculoviruses in which the P10 protein gene promoter is inactive.

In the baculoviruses AcNPV (*Autographa californica* Nuclear Polyhedrosis Virus) and GmNPV (*Galleria mellonella* Nuclear Polyhedrosis Virus), the P10 polypeptide gene, which is located in EcoRI restriction fragment P, is flanked at the 5' end by a gene coding for a polypeptide designated P26, and in the 3' region by a gene coding for a polypeptide designated P74. The P10 gene promoter is at the 3' end of the P26 gene, in the coding region of the latter.

The Inventors have carried out the deletion of the region bounded by an XhoI site (position +569 of the P26 gene) and a BglII site (position +152 of the P10 gene), and then religated these sites after repair with the Klenow enzyme. The region corresponding to the promoter and to the 5' end of P10 is thereby deleted. A chimeric gene consisting of the first 569 bases of P26 and the last 130 bases of P10 is obtained; this gene is functional, and the baculoviruses modified in this way are perfectly viable and produce more polyhedrin than the wild-type virus.

According to a preferred embodiment of the present invention, the genome of the said modified baculovirus is devoid of a DNA sequence bounded by the XhoI site located at +569 bp from the ATG initiation codon of the sequence coding for the P26 polypeptide and the BglII site located at +152 bp from the ATG initiation codon of the sequence coding for the P10 polypeptide.

The invention also encompasses the following baculoviruses, in which the polyhedrin gene promoter is inactive:

a modified baculovirus whose genome is devoid of a DNA sequence bounded by the EcoRV site located at −95 bp and the SspI site located at +910 bp from the ATG initiation codon of the polyhedrin sequence;

a modified baculovirus whose genome is devoid of a DNA sequence bounded by the EcoRV site located at −95 bp and the KpnI site located at +633 bp from the ATG initiation codon of the polyhedrin sequence;

a modified baculovirus whose genome is devoid of a DNA sequence bounded by the EcoRV site located at −95 bp and the Eco47III site located at +733 bp from the ATG initiation codon of the sequence coding for polyhedrin.

The Inventors have established that the baculoviruses thus modified multiply well in cell culture, and no longer produce the protein whose promoter is inactivated but, in contrast, synthesise in larger amounts than the wild-type baculovirus the protein whose promoter is active.

According to another preferred embodiment of the present invention, the modified baculoviruses contain a marker sequence, placed under the control of the active promoter.

In the sense of the present invention, "marker sequence" is understood to mean a sequence whose expression confers a readily identifiable phenotype on the modified baculovirus. The subsequent insertion of an exogenous sequence within the said sequence leads to abolition of the said phenotype, thereby permitting selection of the baculoviruses which have integrated the said exogenous sequence.

According to an especially advantageous arrangement of this embodiment, the marker sequence consists of the sequence coding for polyhedrin, which sequence is placed under the control of the P10 protein gene promoter. The modified baculoviruses obtained in this way recover their ability to produce inclusions. A baculovirus strain obtained according to this arrangement was deposited on 17th Jul. 1990 with the Collection Nationale de Microorganismes (National Collection of Microorganisms) held by the Pasteur Institute in Paris. This strain bears deposit number I-978.

According to another especially advantageous arrangement of this embodiment, the modified baculovirus contains the sequence coding for β-galactosidase, placed under the control of the active promoter (P10 protein or polyhedrin). The baculoviruses modified in this way have the property of forming blue viral plaques in the presence of the substrate X-gal.

The use of baculoviruses obtained according to one of the two foregoing arrangements makes it possible, during subsequent insertion of a foreign gene, to select readily the recombinant viruses which have integrated the said foreign gene within the polyhedrin gene or within that for β-galactosidase. In effect, in the first case, the said recombinant viruses no longer form polyhedra; in the second case, they form white plaques instead of blue plaques.

To obtain modified baculoviruses which are usable for obtaining the expression vectors according to the invention, inactivation of one of the strong late promoters present in the genome of the wild-type baculovirus is carried out by any suitable means.

For example, inactivation of the polyhedrin promoter, or of the P10 protein promoter, is accordingly carried out by excision of a DNA fragment comprising the said promoter.

The excision of the said DNA fragment may be performed using restriction enzymes.

It is self-evident that other methods, such as, for example, conventional methods employing techniques of homologous recombination, may be used in order to carry out the excision of the desired DNA fragment.

The inactivation of one or other of the two promoters may also be performed by mutagenesis of sequences participating in the activity of the said promoter, for example as described in the publication of RAKIN et al., cited above.

Loaded expression vectors according to the invention may be obtained from modified baculoviruses by various methods known per se, for example, and without implied limitation, using transfer vectors such as those described in European Patent Applications 127,839 and 340,359, or alternatively by direct insertion as described in European Patent Application 345,152.

The sequence coding for the exogenous protein which it is desired to have expressed is inserted under the control of the active promoter; the sequence which, in the wild-type baculovirus is normally placed under the control of the said promoter may be totally or partially excised, and replaced by the sequence coding for the exogenous protein.

A better understanding of the present invention will be gained from the additional description which follows, which relates to examples of construction of the modified baculoviruses and the expression vectors according to the invention. It is, nevertheless, self-evident that these examples are given only by way of illustration of the present invention, and in no way constitute a limitation of the latter.

EXAMPLE 1

Construction of a modified baculovirus devoid of the promoter and of the structural gene for polyhedrin The protocols used in this example and those which follow make use of conventional techniques of genetic engineering such as those described by MANIATIS et al., [Molecular cloning: A Laboratory Manual; Cold Spring Harbor Laboratory, 1982]. The conditions peculiar to each experiment are, if appropriate, specified in the corresponding example.

Modified baculoviruses according to the invention are obtained by partial digestion of wild-type baculovirus DNA with two restriction enzymes, one of whose cleavage sites is located upstream of the polyhedrin promoter, and the other downstream of the said promoter, either in the sequence coding for polyhedrin or downstream of the said sequence.

Total genomic DNA of a baculovirus belonging to the strain *Autographa californica* is cut successively with the enzymes EcoRV and Eco47III according to the partial digestion technique described in "Current Protocols in Molecular Biology", Ausubel et al., Eds., published by Geene Publishing Associates and Wiley Interscience (section 3.1.6).

The conditions chosen are as follows:

Cleavage with EcoRV

10 μg of baculovirus DNA are diluted in 100 μl of 10 mM tris-HCl buffer (pH 7.5), 10 mM $MgCl_2$, 150 mM NaCl.

3 units of enzyme per μg of DNA are added. Successive dilutions are carried out in the same buffer and, for each dilution, after incubation for 15 minutes at 37° C., the restriction products are analysed on agarose gel in order to determine the dilution which gives only one cleavage per molecule of viral DNA.

The dilution adopted is, for EcoRV, 1/27.

Cleavage with Eco47III

The experimental conditions are the same as those described for EcoRV.

The dilution adopted is 1/54.

The molecules cut with EcoRV and Eco47III are provided with blunt ends, which enables their ligation to be carried out directly in order to obtain molecules of circular viral DNA.

The resulting viral DNA molecules are used, after purification, to transfect cultures of *Spodoptera frugiperda* cells (SF9 strain, ATCC No. CRL 1711), according to the protocol described by GRAHAM and VAN DER ERB, [Virology, 52, 305–309 (1973)].

Under these conditions, the DNA molecules carrying the desired deletion are infectious, and give viruses which produce plaques not forming polyhedra.

These viruses are referred to as $pob^-$ viruses.

EXAMPLE 2

*Aurographa californica* baculovirus genomic DNA is digested successively with the enzymes KpnI and EcoRV under the conditions described in Example I [sic], except that the Kpn I treatment is performed in a buffer without NaCl, and at a dilution of 1/9. The molecules are then religated and used to transfect *Spodoptera frugiperda* cultures, as described above.

EXAMPLE 3

The procedure is as described in Example 1 or 2, except that the wild-type baculovirus used belongs to the strain *Galleria mellonella.*

EXAMPLE 4

Insertion of the sequence coding for β-galactosidase under the control of the promoter of the P10 protein The Eco R1 [sic] restriction fragment P, obtained from the genome of the wild-type *Autographa californica* baculovirus and which contains the structural gene for the P10 protein, is inserted into the multi-site linker of plasmid pUC9 at the Eco R1 site. This fragment contains a single BglII site located at +152 bp with respect to the ATG codon of the P10 gene. A BamHI fragment comprising the greater part of the β-galactosidase gene (which possesses a BamHI site downstream of its own ATG) is inserted at the BglII site; the reading frames of the beginning of the P10 protein and of β-galactosidase are thus in phase.

The plasmid obtained (D3PZ) hence possesses the beginning of the P10 protein gene and the β-galactosidase gene. *Spodoptera frugiperda* cells are cotransfected with plasmid D3PZ and $pob^-$virus DNA (1 μg of D3PZ; 0.5 μg of pob–DNA; the protocol is identical to that of Example 1) and the recombinant ($pob^-$ β-galactosidase) baculoviruses which form blue plaques in the presence of X-gal are selected. The recombinant viruses obtained express β-galactosidase in very large amounts, as shown in Example 7 below.

EXAMPLE 5

Introduction of the structural gene for polyhedrin in place of the structural gene for the P10 protein The Eco R1 fragment I of the genomic DNA of the baculovirus *Autographa californica*, containing the polyhedrin gene, was cloned into the multi-site linker of plasmid pUC18 at the EcoRI site. A PvuII site was introduced at –2 bases with respect to the ATG codon of the sequence coding for polyhedrin.

Furthermore, a plasmid of [sic] containing the Eco R1 fragment P of the genome of the baculovirus of *Autographa californica* (cf. Example 4) is opened at the BglII site. After the action of the enzyme Ba131 and then of Klenow polymerase, a BglII linker is introduced. A plasmid referred to as pGH 80–82, devoid of the greater part of the sequence coding for the P10 protein and carrying a BglII site at position −4 with respect to the ATG of the P10 protein, is thereby obtained.

The structural gene for polyhedrin, excised from plasmid pUC18 using the restriction enzymes PvuII and Eco47III, is introduced at the BglII site of plasmid pGH 80–82 after restoration of the blunt ends with Klenow polymerase.

The plasmid obtained, referred to as pGH 80–82 $ob^+$, is used, with the $pob^-$ virus obtained in Example 1, to cotransfect *Spodoptera frugiperda* cells.

The recombinant ($pob^-$ $ob^+$) viruses which form polyhedra are selected.

A strain of recombinant ($pob^-ob^+$) viruses was deposited on 17th Jul. 1990 with the Collection Nationale de Microorganismes at 28 Rue de Docteur Roox, 75724 Paris Cedex 15 (FRANCE) under number 1–978.

the β-galactosidase gene is fused to that of the P10 polypeptide (Acp10Z). The recombinant virustis of the conventional type (it possesses both strong promoters and manufactures polyhedra);

the β-galactosidase gene was fused to that for the P10 polypeptide (D3PZ). The recombinant virus, of the $pob^-$ type, no longer possesses the promoter or the gene for polyhedrin.

These different recombinant viruses were used to transfect *Spodoptera frugiperda* cells.

At the following times: 24 h, 48 h, 72 h after infection, the β-galactosidase activity is measured in the culture supernatant and in the cells themselves, using ONPG as a chromogenic substrate. 3 measurements are carried out for each point.

The results are summarised in Table I below:

TABLE I

| | 24 h | | 48 h | | 72 h | |
|---|---|---|---|---|---|---|
| | Sn | Cel | Sn | Cel | Sn | Cel |
| Polyhedrin-β-Gal | 0 | 225 ± 15 | 770 ± 25 | 17133 ± 1400 | 2735 ± 600 | 36732 ± 1133 |
| AcP10Z | 0 | 275 ± 10 | 235 ± 20 | 19066 ± 600 | 1105 ± 210 | 42999 ± 4135 |
| D3PZ | 0 | 300 ± 15 | 295 ± 70 | 24733 ± 640 | 2080 ± 1200 | 46532 ± 2400 |

[β-Gal unit = 1000 ($OD_{420}$)/time (min) × volume (ml)
Cel = cells
Sn = supernatant 48 hours after transfection, the culture supernatant contains very little activity (cell lysis has not yet taken place). The D3PZ cells contain 1.4 times as much activity as the polyhedrin-β-Gal cells. At 72 hours, despite a cell lysis which becomes substantial, D3PZ still possesses more activity than the other constructions.

EXAMPLE 6

Cloning of the acetylcholinesterase (Ache) gene of Drosophila

A cDNA fragment obtained from Ache mRNA was cloned beforehand into a plasmid pEMBL8 between the Sma I and Eco R1 sites. From the said plasmid, the Ache gene is excised by the action of the enzymes FspI (site at −14 bp from the ATG codon of Ache) and SacI (site at +117 bp from the termination codon of Ache).

After treatment with phage T4 DNA polymerase, the fragment obtained is inserted into plasmid pGH 80–22 at the BglII site, the ends of which have been rendered blunt beforehand with Klenow polymerase. The plasmid obtained is referred to as pGH 80–22 Ache.

This plasmid is used either to cotransfect cells with a $pob^-$ $ob^+$ virus DNA: the recombinants which no longer form polyhedra are then selected;

or to cotransfect cells with a $pob^-$ β-galactosidase virus DNA: in this case, the recombinant viruses selected will be those which form white plaques.

EXAMPLE 7

Expression of the β-galactosidase gene: Comparison between the recombinant baculoviruses known in the prior art and the expression vectors according to the invention Three constructions-were carried out:

the β-galactosidase gene is "fused" to that for polyhedrin (Polyhedrin-β-Gal). The recombinant virus is of the conventional-type (it possesses both strong promoters);

EXAMPLE 8

Construction of a modified baculovirus devoid of the promoter and of the structural gene for the P10 protein Total genomic DNA of a baculovirus belonging to the strain *Autographa californica* is cut successively with the enzymes XhoI and BglII, according to the partial digestion technique described in Example 1. The conditions employed are as follows:

Cleavage with XhoI

10 μg of baculovirus DNA are diluted in 100 μl of 50 mM tris-HCl buffer (pH 7.5), 10 mM $MgCl_2$, 100 mM NaCl.

3 units of enzyme per μg of DNA are added. Successive dilutions are carried out in the same buffer and, for each dilution, after incubation for 15 minutes at 37° C. the restriction products are analysed on agarose gel in order to determine the dilution which gives only one cleavage per molecule of viral DNA.

The dilution adopted is, for XhoI, 1/27.

Cleavage with BglII

10 μg of baculovirus DNA are diluted in 100 μl of 10 mM tris-HCl buffer (pH 7.5), 10 mM MgCl, 50 mM NaCl.

The other experimental conditions are the same as those described for XhoI.

The dilution adopted is 1/54.

The ends of the molecules cut with XhoI and BglII are repaired with the Klenow enzyme before their ligation is carried out.

The resulting viral DNA molecules are used to transfect cultures of *Spodoptera frugiperda* cells.

Under these conditions, the DNA molecules carrying the desired deletion are infectious.

These viruses are referred to as $P10^-$ viruses; they produce more polyhedrin than the wild-type virus.

EXAMPLE 9

Insertion of the β-galactosidase gene into a modified baculovirus according to the invention A transfer vector obtained from a pUC8 plasmid and comprising the EcoRI fragment 1 of the baculovirus (cf. Example 5), which contains a single BamHI site, at +171 bases from the ATG codon of the polyhedrin gene, is used for this construction.

A BamHI fragment of the β-galactosidase gene (cf. Example 4) is inserted at the BamHI site of the said transfer vector.

The vectors thereby obtained are used, together with modified $P10^-$ baculoviruses obtained by the protocol described in Example 8, to cotransfect *Spodoptera frugiperda* cells.

The baculoviruses which have integrated the β-galactosidase gene no longer form polyhedra but synthesise β-galactosidase, which is readily detectable and quantifiable by specific staining with the chromogenic substrate X-gal.

The production of β-galactosidase by the modified baculoviruses thereby obtained was compared, as described in Example 7, with that of a similar construction obtained from wild-type baculoviruses (possessing the P10 protein promoter and that of polyhedrin). The level of β-galactosidase produced 48 hours after infection is 25% higher in the modified baculoviruses devoid of the P10 protein promoter than in the wild-type baculoviruses.

We claim:

1. An expression vector comprising a modified nuclear polyhedrosis virus (NPV) baculovirus in which the promoter of the P10 or polyhedrin gene present in the genome of the wild-type is inactive, and wherein a nucleotide sequence placed under control of the promoter which is active in the said modified NPV is different from the corresponding nucleotide sequence of the wild-type NPV.

2. The expression vector according to claim 1, wherein the inactive promoter is that of the polyhedrin gene and the active promoter is that of the P10 protein gene.

3. The expression vector according to claim 1, wherein the inactive promoter is that of the P10 protein gene and the active promoter is that of the polyhedrin gene.

4. The expression vector according to any one of claims 1 to 3, wherein said expression vector contains a marker sequence, placed under control of the active promoter.

5. The expression vector according to claim 2, wherein the modified NPV is *Autographa californica* NPV (AcNPV), the genome of which is devoid of a DNA sequence bounded by the EcoRV site located at −95 bp and the KpnI site located at +633 bp from the ATG initiation codon of the polyhedrin sequence.

6. The expression vector according to claim 2, wherein the modified NPV is *Autographa californica* NPV (AcNPV), the genome of which is devoid of a DNA sequence bounded by the EcoRV site located at −95 bp and the Eco47III site located at +733 bp from the ATG initiation codon of the sequence coding for polyhedrin.

7. The expression vector according to claim 3, wherein the modified NPV is *Autographa californica* NPV (AcNPV), the genome of which is devoid of a DNA sequence bounded by the XhoI site located at +569 bp from the ATG initiation codon of the sequence coding for the P26 polypeptide and the BglII site located at +152 bp from the ATG initiation codon of the sequence coding for the P10 polypeptide.

8. The expression vector according to claim 4, wherein the marker sequence is the sequence coding for polyhedrin, which sequence is placed under the control of the P10 protein gene promoter.

9. The expression vector according to claim 4, wherein the marker sequence is the sequence coding for β-galactosidase.

10. The expression vector of claim 8, deposited on Jul. 17, 1990 with the Collection Nationale de Microorganisms (National Collection of Microorganisms) under deposit number I-978.

11. A modified AcNPV baculovirus, wherein the genome of said AcNPV is devoid of the P10 protein gene promotor.

12. The baculovirus of claim 11, wherein the genome is devoid of a DNA sequence bounded by the XhoI site located at +569 bp from the ATG initiation codon of the sequence coding for the P26 polypeptide and the BglII site located at +152 bp from the ATG initiation codon of the sequence coding for the P10 polypeptide.

* * * * *

UNITED STATES PATENT AND TRADEMARK OFFICE

CERTIFICATE OF CORRECTION

PATENT NO. : 5,571,709

DATED : November 5, 1996

INVENTOR(S) : Devauchelle et al.

It is certified that error appears in the above-indentified patent and that said Letters Patent is hereby corrected as shown below:

On the cover page, Assignee Section which reads:

"Institut National de la Recherche Agronomique"

Should be corrected to read:

--Institut National de la Recherche Agronomique (INRA) and Centre National de la Recherche Scientifique (CNRS)--

Signed and Sealed this

Fifth Day of August, 1997

Attest:

BRUCE LEHMAN

*Attesting Officer*

*Commissioner of Patents and Trademarks*